United States Patent
Ueno

(10) Patent No.: US 8,673,973 B2
(45) Date of Patent: *Mar. 18, 2014

(54) METHOD FOR TREATING OCULAR HYPERTENSION AND GLAUCOMA

(75) Inventor: Ryuji Ueno, Montgomery, MD (US)

(73) Assignee: Sucampo AG (USA) Inc., Bethesda, MD (US)

( * ) Notice: Subject to any disclaimer, the term of this patent is extended or adjusted under 35 U.S.C. 154(b) by 235 days.

This patent is subject to a terminal disclaimer.

(21) Appl. No.: 11/438,290

(22) Filed: May 23, 2006

(65) Prior Publication Data

US 2006/0205725 A1     Sep. 14, 2006

Related U.S. Application Data

(63) Continuation of application No. 10/429,677, filed on May 6, 2003, now Pat. No. 7,074,827.

(60) Provisional application No. 60/420,776, filed on Oct. 24, 2002, provisional application No. 60/421,044, filed on Oct. 25, 2002.

(51) Int. Cl.
      *A61K 31/215*     (2006.01)

(52) U.S. Cl.
      USPC .......................................... 514/530; 514/913

(58) Field of Classification Search
      USPC ................................................. 514/530, 913
      See application file for complete search history.

(56) References Cited

U.S. PATENT DOCUMENTS

| | | |
|---|---|---|
| 2002/0103255 A1 | 8/2002 | Hellberg et al. |
| 2003/0018079 A1 | 1/2003 | Richardson et al. |
| 2004/0097592 A1 | 5/2004 | Morishima et al. |
| 2006/0069162 A1 | 3/2006 | Asada et al. |
| 2008/0221184 A1 | 9/2008 | Yokoyama |

FOREIGN PATENT DOCUMENTS

| | | |
|---|---|---|
| CA | 2 498 233 A1 | 3/2004 |
| EP | 0 603 800 A1 | 6/1994 |
| EP | 1 532 981 A1 | 5/2005 |
| JP | 10-259179 A | 9/1998 |
| JP | 2001-335511 A | 12/2001 |
| JP | 2002-161037 A | 6/2002 |
| WO | 97/23225 A1 | 7/1997 |
| WO | 98/41208 A1 | 9/1998 |
| WO | WO 01/95913 A1 | 12/2001 |
| WO | 02/07731 A2 | 1/2002 |
| WO | WO 02/38158 A1 | 5/2002 |

OTHER PUBLICATIONS

Costagliola, Ciro, et al., "Ocular surface changes induced by topical application of latanoprost and timolol: a short-term study in glaucomatous patients with and without allergic conjunctivitis" Graefe's Arch Clin Exp Ophthalmol (2001), 239: pp. 809-814. XP-002272140.

Noda, Eiichiro, et al., "Blood-aqueous barrier disruption and increment of cystoid macular edema incidence detected by fluorescent angiography caused by ophthalmic solution containing timolol and a preservative thereof in early postoperative pseudophakes", The 105th Annual Meeting of the Japanese Ophthalmology Society, Apr. 19-21, 2001, Place: Pacifico Yokohama.

Xalatan, Pharmacia & Upjohn (4 pages), revised Nov. 2000.
International Search Report, (2010).

*Primary Examiner* — Zohreh Fay

(74) *Attorney, Agent, or Firm* — Sughrue Mion, PLLC

(57) ABSTRACT

Provided is a method for treating ocular hypertension and glaucoma with reduced side effects such as keratoconjunctive disorders and macular edema, which comprises administering an ophthalmic composition comprising latanoprost as an active ingredient thereof to a subject in need of said treatment, wherein the ophthalmic composition contains substantially no benzalkonium chloride.

12 Claims, No Drawings

# METHOD FOR TREATING OCULAR HYPERTENSION AND GLAUCOMA

RELATED APPLICATIONS

This is a continuation of application Ser. No. 10/429,677 filed May 6, 2003, now U.S. Pat. No. 7,074,827, which claims benefit of U.S. Provisional Application No. 60/420,776 filed Oct. 24, 2002, and U.S. Provisional Application No. 60/421,044 filed Oct. 25, 2002; the above noted prior applications are all hereby incorporated by reference.

TECHNICAL FIELD

The present invention relates to a method for treating ocular hypertension and glaucoma with reduced side effects, which comprises administering an ophthalmic composition comprising latanoprost as an active ingredient thereof, which contains substantially no benzalkonium chloride.

BACKGROUND ART

Preservatives used in ophthalmic compositions are required to exhibit a sufficient antimicrobial effect on bacteria and fungi as well as a high degree of safety such that inducing no or small affection on eye tissues such as corneal epithelium. In addition to the original purposes as above, the preservatives themselves are required to be stable. Further, the preservatives are required to homogenize and stabilize the composition by interacting with the ingredients, for example, by homogeneously dispersing or dissolving the ingredients into the vehicle or base. Benzalkonium chloride is a preservative most commonly used in commercially available ophthalmic solutions.

However, preservatives are known as the major etiology of keratoconjunctive disorders, and for safety purpose, it is preferred that the concentration of a preservative such as benzalkonium chloride is below 0.01%. According to recent reports, preservatives contained in ophthalmic solution cause blood-aqueous barrier disruption and macular edema, especially cystoid macular edema (hereinafter referred to as "CME") (The 105th General Assembly of Japan Ophthalmological Society, P. 112, OSN Supersite, Top Stories, 97/10/02, the contents are herein incorporated by reference).

Xalatan® ophthalmic solution, which has been marketed as a drug for treating ocular hypertension and glaucoma, contains latanoprost as an active ingredient thereof. Xalatan® ophthalmic solution contains benzalkonium chloride as a preservative at a concentration of 0.02% (package insert of Xalatan®), and side effects such as keratoconjunctive disorders and CME caused by such high concentration of the preservative have been the problem.

However, since latanoprost is highly fat-soluble, it has been believed to be difficult to prepare homogeneous and stable latanoprost ophthalmic composition without benzalkonium chloride. To the present, latanoprost ophthalmic composition containing no or less than 0.02% of benzalkonium chloride has not been provided as a commercially available product.

SUMMARY OF THE INVENTION

The present invention relates to a method for treating ocular hypertension and glaucoma, which comprises administering an ophthalmic composition comprising latanoprost as an active ingredient thereof to a subject in need of said treatment, wherein the ophthalmic composition contains substantially no benzalkonium chloride.

Especially, the present invention relates to a method for treating ocular hypertension and glaucoma, which comprises administering an ophthalmic composition comprising latanoprost as an active ingredient thereof to a subject who has ocular hypertension and glaucoma and is in need of treatment or prevention of keratoconjunctive disorders or macular edema, wherein the ophthalmic composition contains substantially no benzalkonium chloride.

The present invention also relates to an ophthalmic composition for treating ocular hypertension and glaucoma comprising latanoprost as an active ingredient thereof, which contains substantially no benzalkonium chloride.

Further, the present invention relates to a use of latanoprost for manufacturing an ophthalmic composition for treating ocular hypertension and glaucoma, which contains substantially no benzalkonium chloride.

The phrase of "the ophthalmic composition contains substantially no benzalkonium chloride" used herein means that the composition contains no benzalkonium chloride, or the composition contains benzalkonium chloride at a concentration that if the amount of benzalkonium chloride in the commercially available Xalatan® ophthalmic solution is reduced below said concentration, homogenous and/or stable solution is difficult to be prepared. In the present invention, the ophthalmic composition may contain Benzalkonium chloride at a concentration of less than 0.02%, preferably 0.01% or less, more preferably 0.005% or less.

The term "treatment" or "treating" used herein includes any means of control such as prevention, care, relief of symptoms, attenuation of symptoms and arrest of progression.

DETAILED DESCRIPTION OF THE INVENTION

The ophthalmic composition of the present invention may be formulated as any dosage form used in the ophthalmic field. For example, the ophthalmic composition may be in liquid form such as solution, emulsion and suspension or semisolid form such as gel and eye ointment. Ophthalmic solution including emulsion and suspension as well as solution is preferably used. The ingredients other than latanoprost may not be particularly limited as far as latanoprost is homogeneously and stably dispersed or dissolved in the composition. Ophthalmic composition of the present invention may be manufactured according to any of conventional methods.

In case of the composition is an ophthalmic solution, the composition may further contain a dissolving agent. The dissolving agents used in the present invention may be any of conventionally used agents as far as it helps to disperse or dissolve latanoprost homogeneously and stably in an aqueous vehicle containing substantially no benzalkonium chloride. Examples of the dissolving agents may include polyoxyethylenesorbitan higher aliphatic acid monoester such as polysorbate 80, EDTA, boric acid, chlorhexidine gluconate, sodium persulfate, glycerol, concentrated glycerol, polyoxylated caster oil such as polyoxyethylene hydrogenated castor oil 40 and polyoxyethylene hydrogenated castor oil 60, polyoxyl stearate, macrogol, propyleneglycol, povidone, lower alcohol such as ethanol and chlorobutanol Polysorbate 80 and EDTA are especially preferred. The dissolving agent may be used solely or in combination with one or more other dissolving agents.

The ophthalmic composition of the present invention may further contain additives other than the above-listed dissolving agents. According to the present invention, the additives may be any of those conventionally used in the ophthalmic field. Examples of the additives may include osmotic adjusting agents such as sodium chloride, potassium chloride, calcium chloride, sodium bicarbonate, sodium carbonate, magnesium sulfate, sodium hydrogen phosphate, sodium dihydrogen phosphate, dipotassium hydrogen phosphate, borax, sodium hydroxide, hydrochloric acid, isosorbitol, propylene glycol, mannitol, sucrose and glucose; buffering agents such as sodium monohydrogen phosphate and sodium dihydrogen phosphate; thickeners such as saccharides (e.g. lactose and maltose), hyaluronic acids or salt thereof (e.g. sodium hyaluronate and potassium hyaluronate), mucopolysaccharides (e.g. chondroitin sulfate), sodium polyacrylate, carboxyvinyl polymer and crosslinked polyacrylate.

When the composition is an eye ointment, the composition may contain ordinarily used eye ointment bases in addition to the above additives. Examples of eye ointment bases may include oil base such as Vaseline, liquid paraffin, polyethylene, Selen 50, Plastibase, macrogol and a combination thereof, emulsion base in which oil phase and aqueous phase have been emulsified with a surface active agent or the like; and water soluble base such as hydroxypropylmethylcellulose, carboxypropylcellulose and polyethylene glycol.

According to the present invention, it is easy to prepare homogenous and stable latanoprost ophthalmic composition containing less than 0.02% of benzalkonium by admixing a dissolving agent. The ophthalmic composition of the present invention may be prepared as a sterile unit dose type formulation for single use. Furthermore, since the ophthalmic composition of the present invention causes significantly fewer side effects such as keratoconjunctive disorders and CME than commercially available Xalatan® ophthalmic solution, the method of the present invention provides more effective treatment to a subject suffering from keratoconjunctive disorder and/or macular edema such as CME.

The concentration of latanoprost in the composition and dosing frequency may vary according to the type of the subject such as species, age, sex, body weight and general health, symptoms to be treated, desired therapeutic effects, administration route, period of treatment and the like. For example, an ophthalmic solution containing latanoprost at a concentration of 0.00001 to 1%, preferably 0.0001 to 0.1%, more preferably 0.001 to 0.01% may be instilled 1 to 4 times, preferably 1 to 3 times, more preferably 1 to 2 times a day.

In the present invention, the composition may contain pharmaceutically active ingredients other than latanoprost as far as they are not contrary to the objects of the present invention. Examples of the pharmaceutically active ingredients may include parasympathomimetic agents such as pilocarpine and carbachol; cholinesterase inhibitors such as phy- sostigmine salicylate, distigmine bromide and echothiopate iodide; sympathomimetic agents such as epinephrine, dipivalylepinephrine, clonidine, p-aminoclonidine and brimonidine; β-adrenergic blockers such as betaxolol, levobunolol, timolol and carteolol; prostaglandin compounds such as isopropyl unoprostone, travoprost and bimatoprost; tropicamide and the like. Among these pharmaceutically active agents, timolol is especially preferable. In the preparation that contains two or more active ingredients, the amount of each ingredient may be determined appropriately according to the therapeutic effects and safety of each ingredient.

The present invention will be described in more detail with reference to the following examples, which is not intended to limit the scope of the present invention.

EXAMPLE

Latanoprost was mixed in various additives at the amount shown in table 1 below respectively to prepare 0.005% latanoprost ophthalmic solution. 10 mL of each of the solution was agitated for seven hours and then stood still for 30 minutes. After that, the concentration of the latanoprost in the solutions was measured by HPLC and determined by internal standard method with one point calibration curve.

$$\text{Concentration of latanoprost } (mg/mL) = 0.04 \times W_s \times \frac{Q_T}{Q_S}$$

Ws: The amount of latanoprost in the standard preparation (mg)

Qs: Peak area ratio of latanoprost in the standard preparation to the internal standard Qt: Peak area ratio of latanoprost in the test preparation to the internal standard The results are shown in Table 1 below.

TABLE 1

Concentration of latanoprost in the various latanoprost ophthalmic solution

| Test No. | Amount of additives (%) | | | | | | Conc.*3 (mg/mL) | Homogeneity*4 |
|---|---|---|---|---|---|---|---|---|
| | BAC*1 | P80*2 | EDTA | NaH₂PO₄H₂O | Na₂HPO₄ | NaCl | | |
| 1 | — | — | — | 0.46 | 0.47 | 0.41 | 0.04415 | 88.3 |
| 2 | — | 0.2 | — | 0.46 | 0.47 | 0.41 | 0.04998 | 100.0 |
| 3 | 0.01 | — | — | 0.46 | 0.47 | 0.41 | 0.04863 | 97.3 |
| 4 | 0.01 | 0.2 | — | 0.46 | 0.47 | 0.41 | 0.04994 | 99.9 |
| 5 | 0.01 | 0.2 | 0.05 | 0.46 | 0.47 | 0.41 | 0.04993 | 99.9 |

*1BAC: Benzalkonium chloride
*2P80: polysorbate 80
*3concentration of latanoprost
*4ratio (%) of latanoprost in the solutions 30 minutes after the agitation for seven hours to initially used latanoprost As is shown in Test Nos. 1 and 2, the homogeneity of latanoprost in the ophthalmic solution without benzalkonium chloride was improved by admixing polysorbate 80 (88.3% to 100.0%).

As is shown in Test Nos. 3-5 of Table 1, the homogeneity of latanoprost in the ophthalmic solution with 0.01% of benzalkonium chloride was improved by admixing polysorbate 80 or, polysorbate 80 and EDTA (97.3% to 99.9%).

These results suggested that the homogeneity and stability of latanoprost ophthalmic solution were improved by admixing a dissolving agent.

What is claimed is:

1. A method for treating ocular hypertension and glaucoma, which comprises administering an ophthalmic solution consisting essentially of latanoprost as the sole active ingredient thereof which reduces intraocular pressure and 0.005% or less of benzalkonium chloride to a subject in need of said treatment.

2. The method as described in claim 1, wherein the ophthalmic solution contains a dissolving agent.

3. The method as described in claim 2, wherein the dissolving agent is polysorbate 80 and/or EDTA.

4. The method as described in claim 1, wherein the ophthalmic solution is formulated as a single-unit dose preparation.

5. A method for treating ocular hypertension and glaucoma, which comprises administering an ophthalmic solution consisting essentially of latanoprost as the sole active ingredient thereof which reduces intraocular pressure and 0.005% or less of benzalkonium chloride to a subject who has ocular hypertension and glaucoma and is in need of treatment or prevention of keratoconjunctive disorders or macular edema.

6. The method as described in claim 5, wherein the ophthalmic solution contains a dissolving agent.

7. The method as described in claim 6, wherein the dissolving agent is polysorbate 80 and/or EDTA.

8. The method as described in claim 5, wherein the ophthalmic solution is formulated as a single-unit dose preparation.

9. The method as described in claim 1, wherein the ophthalmic solution contains absolutely no benzalkonium chloride.

10. The method as described in claim 5, wherein the ophthalmic solution contains absolutely no benzalkonium chloride.

11. The method as described in claim 4, wherein the single-unit dose preparation is a sterile unit dose formulation for single use.

12. The method as described in claim 8, wherein the single-unit dose preparation is a sterile unit dose formulation for single use.

* * * * *